United States Patent [19]

Sagramora

[11] 4,336,398
[45] Jun. 22, 1982

[54] PROCESS FOR THE PREPARATION OF BASIC ESTERS OF SUBSTITUTED HYDROXYCYCLOHEXANECARBOXYLIC ACIDS

[75] Inventor: Giorgio Sagramora, Padua, Italy

[73] Assignee: Laboratorio Guidotti & C. S.p.A., Pisa, Italy

[21] Appl. No.: 96,938

[22] Filed: Nov. 23, 1979

[30] Foreign Application Priority Data

Nov. 24, 1978 [IT] Italy .................. 30163 A/78

[51] Int. Cl.³ .................................. C07C 69/76
[52] U.S. Cl. .......................... 560/59; 560/118
[58] Field of Search ................... 560/118, 59

[56] References Cited

U.S. PATENT DOCUMENTS 3,700,675 10/1972 Turbanti .................. 560/59

FOREIGN PATENT DOCUMENTS 160478 4/1952 Australia ................... 560/59
539593 4/1957 Canada ..................... 560/59

*Primary Examiner*—Paul J. Killos
*Attorney, Agent, or Firm*—McAulay, Fields, Fisher, Goldstein & Nissen

[57] ABSTRACT

The yield of compounds having the general formula:

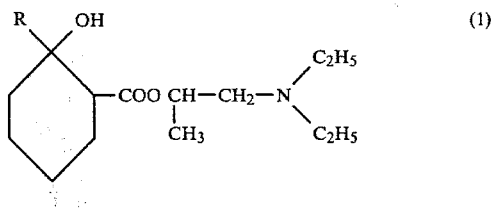

wherein R represents

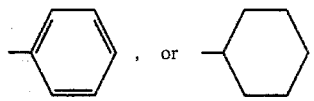

in the process comprising reacting a substituted hydroxycyclohexanecarboxylic acid with an aminoisopropyl chloride, is highly improved by heating the reaction mixture to 160° to 240° C. for at least 3 hours, and distilling under reduced pressure the resulting product. Thus the content of the undesired isomer is reduced to less than 1–1.5%.

5 Claims, No Drawings

PROCESS FOR THE PREPARATION OF BASIC ESTERS OF SUBSTITUTED HYDROXYCYCLOHEXANECARBOXYLIC ACIDS

The present invention relates to the preparation of basic esters of substituted hydroxycyclohexanecarboxylic acids, having the following general formula:

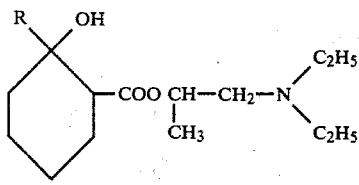

wherein R represents

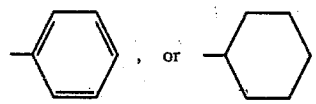

More specifically, the present invention relates to an improved process for the preparation of 2-(diethylamino)-1-methylethyl-cis-1-hydroxy-[bicyclohexyl]-2-carboxylate, and of 2-(diethylamino)-1-methylethyl-cis-2-hydroxy-2-phenyl-cyclohexanecarboxylate.
The subject esters, which are known for their anti-spastic activity, are part of a family of basic esters, disclosed in the U.K. patent specification No. 1,167,386 and in the German Pat. No. 1,618,624.

According to the known prior art, for the preparation of these esters a general method is used, comprising reacting the potassium salt of a substituted hydroxycyclohexane carboxylic acid with an aminoalkyl chloride:

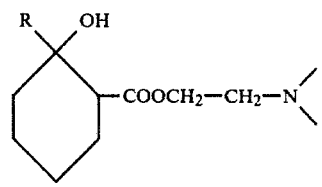

There are also known two alternative methods, having limited practical importance, due to the poor yields of the desired product, and consisting precisely in the reaction of the potassium salt of a substituted hydroxycyclohexanecarboxylic acid with an alkylene dihalide and subsequent reaction of the alkylhalogenated ester with a secondary amine, or in the chlorination, under mild conditions, of a substituted hydroxycyclohexanecarboxylic acid and subsequent reaction of the related acylchloride with an amino alcohol.

Among all these methods, the only one of effective interest from the industrial point of view is the first mentioned process. A detailed description of this method, referred to one of the esters, is given in the example IV of the U.K. patent specification No. 1,167,386, already referred to.

By applying this method to the compounds of the present invention, it is possible to obtain a product fulfilling the analytical requisites, provided that the raw product, of oily nature, is subjected to two subsequent distillation steps, instead of only one, or to a fractionation by a rectification, these operations certainly affecting the yield.

In the case of the subject compounds (as represented by the formula (1), during the reaction of cis-1-hydroxy-[bycyclohexyl]-2-carboxylic acid or of cis-2-hydroxyphenyl-cyclohexanecarboxylic acid and 1-diethylamino-2-chloropropane in the presence of an acceptor of hydrogen chloride (such as, for instance, $K_2CO_3$, NaOH, $KOCH_3$, $NaOCH_3$, etc.), two products are always formed, which, for sake of convenience, are identified as A and B, according to the following scheme:

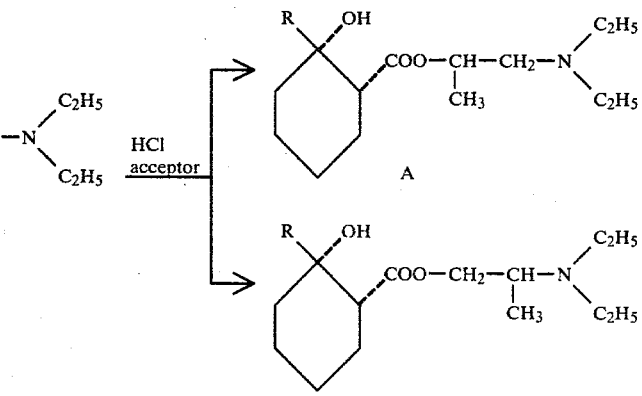

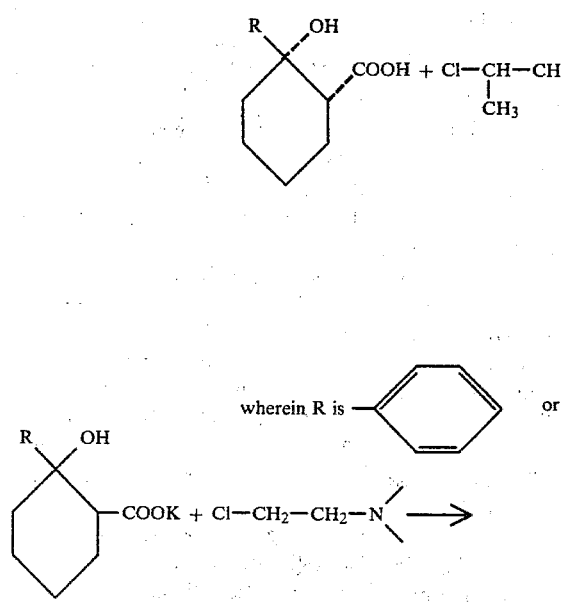

wherein R is 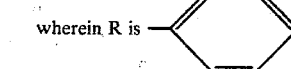 or 

This is due to the fact that, as it is well known, 1-diethylamino-2-chloropropane does react in the cyclic form:

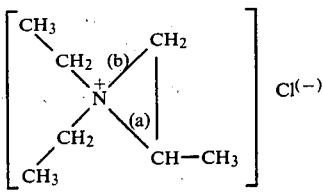

in which the breakage of the bond is possible either in the position (a), to give place to the product A, and in the position (b), giving thus place to the product B.

By varying the solvent and the reaction temperature, different proportions of product A and of product B are obtained, but the amount of the undesired isomer B cannot be lowered below 28–30%, when $R=C_6H_{11}$, and below 16–17%, when $R=C_6H_5$, respectively. The influence of the solvent and of the temperature on the composition of the reaction product is shown by the following results, relating to the reactions carried out with cis-1-hydroxy-[bicyclohexyl]-2-carboxylic acid:

in anhydrous toluene, using $K_2CO_3$ as the hydrogen acceptor

| Product A | 53.5% | ⎫ | |
|---|---|---|---|
| Product B | 46.5% | ⎬ | 25° C. |
| Product A | 57.0% | ⎫ | |
| Product B | 43.0% | ⎬ | 100° C. | in anhydrous dimethyl formamide, using $K_2CO_3$ as the hydrogen acceptor:

| Product A | 63.0% | ⎫ | |
|---|---|---|---|
| Product B | 37.0% | ⎬ | 25° C. | in isopropanol, using potassium methylate as the hydrogen acceptor:

| Product A | 64.5% | ⎫ | |
|---|---|---|---|
| Product B | 35.5% | ⎬ | 25° C. |
| Product A | 72.0% | ⎫ | |
| Product B | 28.0% | ⎬ | 80° C. | in isopropanol, using $K_3CO_3$ as the hydrogen acceptor:

| Product A | 70.0% | ⎫ | |
|---|---|---|---|
| Product B | 30.0% | ⎬ | 80° C. |

The separation of the product A from the product B, as obtained by the above described reaction, can be carried out by fractionated distillation.

Of course, the yield of the process, referred to the product A, which is the desired one, is always remarkably reduced in comparison with the theoretical value. The main purpose of the present invention is therefore that of solving the above mentioned problem, which purpose is attained by a process characterized in that the reaction mixture, comprising product A and product B, is heated to a temperature of between 160° C. and 240° C. for a time of at least 3 hours, and then fractionately distilled at a temperature not lower than that of the said heating step.

In fact it has been assessed that, by the process of the present invention, the final product has a highly reduced content of product B which, under optimum conditions, is not higher and often lower than 1%, when $R=C_6H_{11}$, and then 1.5%, when $R=C_6H_5$.

The advantages of the process according to the present invention are per se readily appreciated: instead of being obliged to separate from the reaction mixture the undesired isomer, and moreover through a difficult operation which causes the yields to be reduced, the reaction mixture undergoes a further treatment step by which the yield of the desired compound is almost the theoretical one.

According to the practice of the process according to the present invention, the mixture of compounds A and B, after the normal isolation steps, is heated to a temperature of between 160° and 240° C., preferably to a temperature not less than 180° C., for time of at least 3 hours, the upper limit being the time beyond which the desired compound A is decomposed. In fact it has been found that the heating temperature and the heating time are inversely proportional, whereby yields close to 100% of the theoretical value are obtained both by heating at 180° C. for six hours and subsequent distillation at the same temperature, and by heating at 220°–230° C. for 3 hours and subsequent fractioned distillation at 230°–240° C.

The following examples, having only illustrative but not limitative meaning, detailedly disclose the process of the present invention.

EXAMPLE 1

200 g of cis-1-hydroxy-[bicyclohexyl]-2-carboxylic acid, dissolved in 1000 mls of isopropyl alcohol are supplemented with 188 g of anhydrous potassium carbonate. The mixture is heated to reflux (82° C.) and, by maintaining this temperature, 164 g of 1-diethylamino-2-chloropropane hydrochloride, dissolved in 500 mls of isopropyl alcohol, are added.

Upon the addition is completed, the reaction mixture is maintained under reflux for 7 hours.

The reaction mixture is cooled and the salts (KCl and KHCO$_3$) are filtered; the isopropilic solution, containing 70% of product A and 30% of product B is subjected to thermal isomerization in the following manner. The solvent is evaporated and the residue (300 g) is dissolved in ethyl ether; the ethereal solution is extracted at 0° C. with diluted hydrogen chloride; the thus separated aqueous phase is made definitely alkaline at 0° C. with diluted sodium hydroxide, and then repeatedly extracted with ethyl ether. The ethereal extracts are repeatedly washed with water until neutral and the solvent is evaporated. The residue (275 g), comprising 70% of product A and 30% of product B is gradually heated from 25° C. to 180° C. during 6 hours, and then distilled under reduced pressure (0.1–0.2 mmHg) in an oil bath at 210° C.

There are obtained 267 g of 2-(diethylamino)-1-methylethyl-cis-1)hydroxy-[bicyclohexyl]-2-carboxylate, with a content of isomer B less than 0.5%.

EXAMPLE 2

The example 1 is repeated until the residue of 275 g is obtained, containing 70% of product A and 30% of product B.

The mixture is gradually heated from 25° C. to 220°-230° C. in three hours and then distilled under reduced pressure (0.1-0.2 mmHg) in an oil bath at 230°-240° C. There are obtained 267 g of product A, with a content of product B less than 1%.

EXAMPLE 3

200 g of cis-2-hydroxy-2-phenyl-cyclohexane carboxylic acid, dissolved in 1000 mls of isopropyl alcohol, are supplemented with 188 g of anhydrous potassium carbonate. The mixture is heated to reflux (82° C.) and, by maintaining the same temperature, there are added 164 g of 1-diethylamino-2-chloropropane hydrochloride, dissolved in 500 mls of isopropyl alcohol. Upon the addition is completed, the reaction mixture is maintained under reflux for 7 hours. The reaction mixture is then cooled and the salts (Kll and KHCO₃) are filtered; the isopropilic solution containing 83.5% of product A and 16.5% of product B is subjected to thermal isomerization in the following manner.

The solvent is evaporated and the residue (296 g) is dissolved in ethyl ether; the ethereal solution is extracted at 0° C. with diluted HCl; the thus separated aqueous phase is made definitely alkaline at 0° C. with diluted sodium hydroxide and then repeatedly extracted with ethyl ether. The ethereal extracts are repeatedly washed with water until neutral and the solvent is evaporated.

The residue (288 g), comprising 83.5% of product A and 16.5% of product B is gradually heated from 25° C. to 180° C. in 6 hours and then distilled under vacuum (0.1-0.2 mmHg) in an oil bath at about 210° C. There are obtained 260 g of product A having a content of product B less than 1.5%.

Like results are obtained by heating from 25° C. to 200° C. and then distilling the mixture under reduced pressure (0.2 mmHg) in an oil bath at about 220°-230° C.

I claim:

1. In a process for the preparation of an ester from mixed esters of substituted hydroxycyclohexanecarboxylic acids involving the thermal isomerization of said mixture of esters, the process comprising preparation of basic esters of substituted hydroxycyclohexanecarboxylic acids having general formula

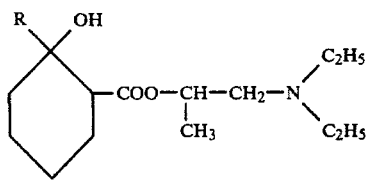

wherein R represents

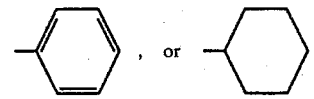

of the type in which a substituted hydroxycyclohexanecarboxylic acid is reacted with a diethylaminoisopropyl hydrochloride, giving place to an isomer mixture comprising the desired basic ester having the formula (1) and the isomer thereof having the formula

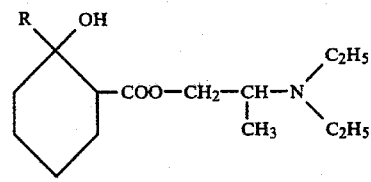

characterized in that the reaction mixture, after isolation, is subjected to thermal isomerization by heating for at least 3 hours at a temperature of between 160° C. and 240° C., and the thus heated mixture is fractionatedly distilled under reduced pressure at a temperature not less than that of said heating.

2. A process according to claim 1, characterized in that said heating takes place from the room temperature to 180° C. in 6 hours and the fractionated distillation takes place at 210° C.

3. A process according to claim 1, characterized in that said heating is effected from the room temperature to 220°-230° C. in 3 hours and the fractionated distillation is carried out at 240° C.

4. A process according to claims 1 to 3, characterized in that said compound of formula (1) is 2-(diethylamino)-1-methylethyl-cis-1-hydroxy-[bicyclohexyl]-2-carboxylate.

5. A process according to claims 1 to 3, characterized in that said compound of formula (1) is 2-(diethylamino)-1-methylethyl-cis-2-hydroxy-2-phenyl-cyclohexanecarboxylate.

* * * * *